United States Patent [19]

Pfeiler

[11] 4,352,986

[45] Oct. 5, 1982

[54] TOMOGRAPHIC APPARATUS FOR THE PRODUCTION OF TRANSVERSE LAYER IMAGES

[75] Inventor: Manfred Pfeiler, Erlangen, Fed. Rep. of Germany

[73] Assignee: Siemens Aktiengesellschaft, Berlin & Munich, Fed. Rep. of Germany

[21] Appl. No.: 158,627

[22] Filed: Jun. 11, 1980

[30] Foreign Application Priority Data

Aug. 8, 1979 [DE] Fed. Rep. of Germany ....... 2932182

[51] Int. Cl.³ ............................................... A61B 6/00
[52] U.S. Cl. ........................................ 378/14; 378/12; 378/24
[58] Field of Search ..................... 250/445 T, 416 TV

[56] References Cited

U.S. PATENT DOCUMENTS 4,146,794 3/1979 Duinker .......................... 250/445 T
4,164,657 8/1979 Duinker et al. ................. 250/445 T Primary Examiner—Alfred E. Smith
Assistant Examiner—T. N. Grigsby
Attorney, Agent, or Firm—Hill, Van Santen, Steadman, Chiara & Simpson

[57] ABSTRACT

The exemplary embodiments disclose a computer tomograph which also is operable for the preparation of an x-ray shadow image. To this end every detector of the radiation receiver is extended in the longitudinal direction so as to permit the formation of the x-ray shadow image by line-by-line scanning of the radiation receiver with the radiation beam having a fan shape in a plane disposed perpendicularly to such longitudinal direction.

3 Claims, 5 Drawing Figures

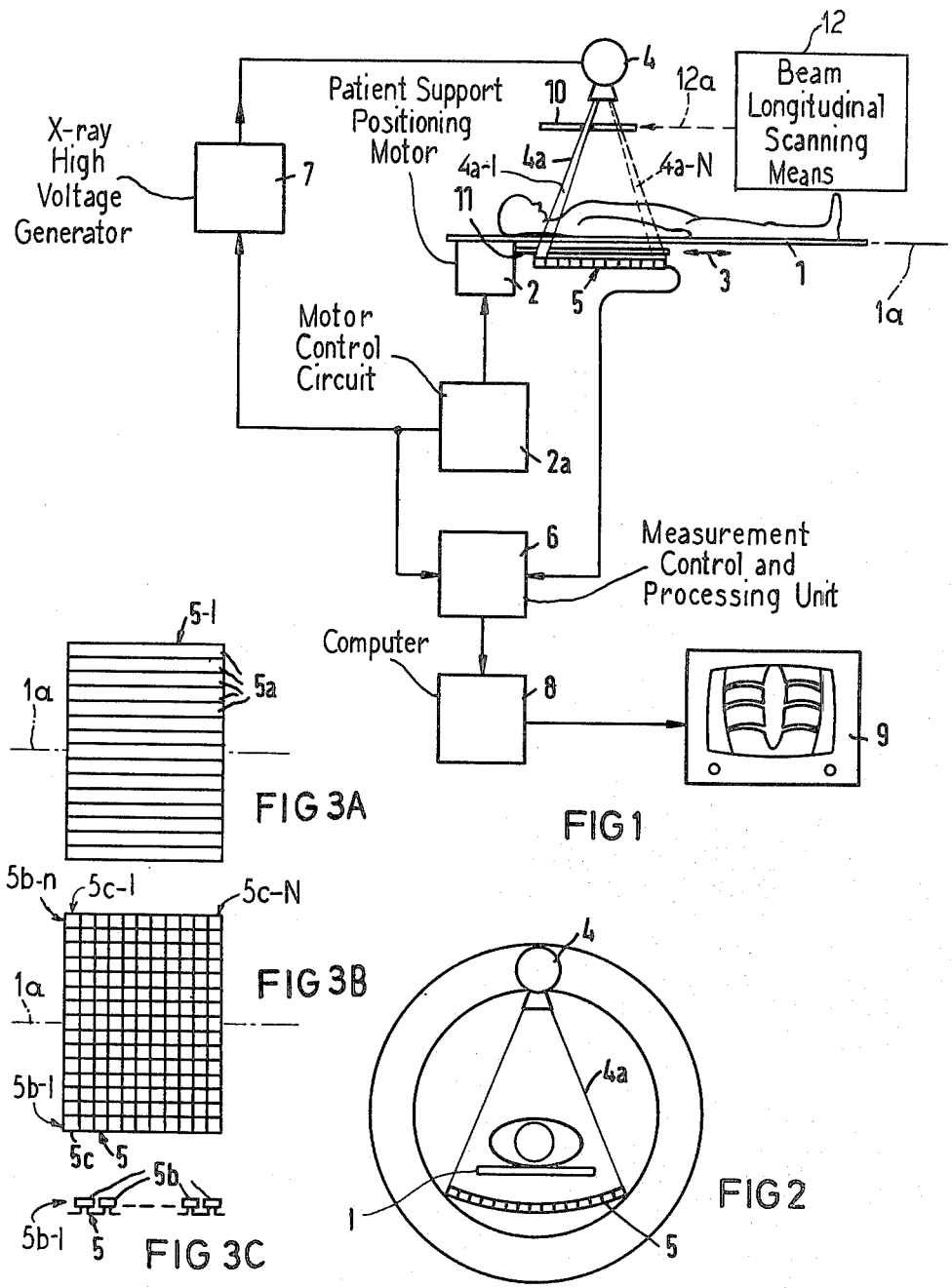

TOMOGRAPHIC APPARATUS FOR THE PRODUCTION OF TRANSVERSE LAYER IMAGES

BACKGROUND OF THE INVENTION

The invention relates to a tomographic apparatus for the production of transverse layer images of a radiography subject, comprising a patient support, comprising a radiation measuring arrangement which includes a radiation source which generates a beam of rays, fan-shaped in the layer plane, penetrating the radiography subject, the cross-sectional extent of said beam of rays perpendicular to the layer plane being equal to the layer thickness, and a radiation receiver which includes a series of detectors disposed transversely relative to the longitudinal direction of the support, and which determines the radiation intensity behind the subject, comprising a rotating device for the measuring arrangement for rotation about an axis extending parallel to the longitudinal axis of the patient support, comprising a measured value converter for the transformation of signals supplied by the radiation receiver into a tomographic image, and further comprising means for scanning a succession of transverse body segments and for calculation and reproduction of an x-ray shadow image whose length corresponds to the distance between the first and last of the transverse body segment scanned and whose width corresponds to the width of the radiation receiver.

A tomographic apparatus of this type is described in the German OS No. 2613809. In the case of this known tomographic apparatus it is possible to prepare two types of photographs; namely, through rotation of the x-ray beam in a plane and generation of output signals of the radiation receiver at different projections, a transverse layer image, a so-called computer tomogram, on the one hand; and, through a relative movement between the measuring arrangement and patient support with the measuring arrangement locked against rotation, an image similar to a conventional x-ray photograph, namely an x-ray shadow image, on the other hand. For the production of an x-ray shadow image, a mechanical movement, either of the patient support or the entire measuring arrangement, is necessary, since the radiation receiver always detects only one line of this x-ray shadow image for a given longitudinal position.

SUMMARY OF THE INVENTION

The object underlying the invention resides in designing a tomographic apparatus of the type initially cited, a so-called computer tomograph, such that, with a stationary radiation receiver and a stationary patient support, the x-ray shadow image can be produced with a simple construction of the apparatus, in particular with regard to the processing electronic system connected to the output side of the radiation receiver.

This object is achieved in accordance with the invention by virtue of the fact that every detector of the radiation receiver is extended in the longitudinal direction of the support so as to permit the formation of the x-ray shadow image through linear scanning along the length of the radiation receiver, with the radiation issuing from the patient in lines running perpendicularly to the longitudinal direction of the support. In the case of the inventive computer tomographic apparatus, movement in a longitudinal direction of the x-ray beam, with a stationary patient support and a stationary radiation receiver, suffices for the production of a shadow image. This movement of the x-ray beam can be produced with the aid of diaphragms or by means of a movement of the x-ray tube.

The invention shall be explained in greater detail below on the basis of an exemplary embodiment illustrated on the accompanying drawing sheet; and other objects, features and advantages will be apparent from this detailed disclosure and from the appended claims.

BRIEF DESCRIPTION OF THE DRAWINGS

FIG. 1 illustrates the parts of a tomographic apparatus which are significant in terms of the invention; and FIGS. 2 and 3 illustrate details of the apparatus according to FIG. 1, FIG. 3 consisting of FIGS. 3A, 3B and 3C.

DETAILED DESCRIPTION

In FIG. 1 a patient support 1 is illustrated which is capable of being moved back and forth by means of a motor 2 in the direction of its longitudinal axis 1a, as indicated by the double arrow 3. In order to produce x-ray images, a radiation measuring arrangement is present which includes an x-ray tube 4 and a radiation receiver 5. The output of the radiation receiver 5 is connected to a measurement control and processing unit 6, which controls an x-ray high voltage generator 7 and a computer 8. Components 6 and 8 together serve as a measured value converter in the tomographic mode for generating a layer image from the raw detector signals supplied by receiver 5. The output of the computer 8 is connected to a television display apparatus 9. In addition, a control circuit 2a for the support positioning motor 2 is present, which is also connected to the x-ray generator 7 and to the unit 6. The measuring arrangement 4, 5 comprises according to FIG. 2 an x-ray tube 4, which generates a fan-shaped x-ray beam 4a which lies in a plane disposed transversely relative to the longitudinal axis 1a of the patient support 1. The beam 4a impinges upon the radiation receiver 5, which is preferably curved about an axis intersecting the focus of the x-ray tube 4 and which axis is parallel to the longitudinal axis 1a of the patient support 1. In the limit case the curvature can be zero; the radiation receiver then lies in a flat plane parallel to the plane of support 1.

The radiation receiver can as one embodiment comprise a series of longitudinally extended detectors 5a, FIG. 3A, which are arranged to form an arcuate receiver 5-l corresponding in configuration to receiver 5, FIG. 2. The longitudinal extent of each detector 5a may correspond to the longitudinal extent of the receiver 5, FIG. 1, parallel to the longitudinal axis 1a of the patient support. The significant feature in the embodiment of FIG. 3A is the length of the detectors which corresponds to the length of the x-ray shadow image to be photographed. (The radiation receiver 5-l is to be arranged as shown for receiver 5 in FIG. 1 so that the beam 4a impinges on successive increments of the length of each detector 5a in the longitudinal scanning mode.) The effect of a long detector can be achieved in a second embodiment through a series-connection of detector elements 5b, FIG. 3C, each detector being of smaller length. The laterally outermost series connections are designated 5b-l and 5b-n in FIG. 3B. In this case, the radiation receiver consists of a plurality of series-connections such as that designated 5b-l in FIG. 3C, arranged to form the arcuate receiver 5, FIGS. 1, 2 and 3B, each series connection of detector elements 5b, FIG. 3C, being disposed parallel to the longitudinal direction of the patient support 1. In every series-connection such as 5b-l, successive detector elements 5b are all connected in series with one output channel of the receiver.

In order to define or limit the x-ray beam 4a in the longitudinal direction of the patient support 1, two slit diaphragms 10 and 11 are present, between which the patient lies. The long dimension of the slits corresponds to the width of receiver 5 or 5-l. Through these slit diaphragms, for the preparation of a computer tomogram, the x-ray beam 4a is so defined in the longitudinal direction parallel to axis 1a of the patient support 1 that the plane of the beam extends perpendicularly to the longitudinal direction of the patient support 1 and irradiates a narrow body layer. In utilizing a series-connection of detector elements 5b such as shown in FIGS. 3B and 3C only one row 5c, FIG. 3B, of detector elements of the radiation receiver 5 is impinged on by x-radiation for each layer to be scanned. During such a layer scanning operation the unit 4, 5 is rotated about the longitudinal axis of the patient. A read out from the active detector row 5c of the radiation receiver 5, takes place during rotation of the measuring arrangement 4, 5, for each of a succession of pulses of the x-ray tube 4. The output signals are supplied by the reset integrator channels of unit 6 to the computer 8 which calculates a transverse layer image therefrom and effects its reproduction on the television monitor 9.

In order to produce an x-ray shadow image of an area of the patient determined by the arcuate extent of the rows 5c and by the dimension of the radiation receiver 5 in the longitudinal direction of the patient support 1; i.e. by the product of the number of detector elements (N) per series-connection, or by the length of a detector 5a, FIG. 3A; and the number of series connections (n), the radiation receiver 5 and the patient support 1 are arrested in a predetermined position, so that the radiation receiver 5 is disposed behind the area of the patient of which an image is to be made. Subsequently, the slit diaphragms 10 and 11 are moved synchronously in the longitudinal direction of the patient support 1 so that the respective slits remain aligned with the focus of tube 4, and the fan beam 4a is shifted incrementally in the longitudinal direction such that, in the case of application of receiver 5-l with long detectors 5a, FIG. 3A, their different surface parts are successively impinged on by x-radiation and the receiver 5-l, FIG. 3A, is progressively scanned in the longitudinal direction, or in the case of receiver 5, FIGS. 1, 2 and 3B, detector elements 5b of the radiation receiver 5 are successively impinged upon by x-radiation; i.e., the radiation receiver 5 is scanned in a linear fashion by x-radiation. The x-ray tube 4 can here be pulsed under the control of unit 6 for the scanning of the individual transverse lines. One thus obtains, from the radiation receiver 5 or 5-l analog output signals which reproduce the radiation attenuation profile of the area of the patient disposed in front of the radiation receiver. The measurement control and processing unit 6 integrates the analog signals and transmits corresponding digital signals to the computer 8 which determines a conventional x-ray shadow image and effects its reproduction on the television monitor 9 (as shown in FIG. 1).

From FIGS. 3A and 3B it is apparent that the radiation receiver to be used in FIGS. 1 and 2 can be formed as an array of extended (or elongated) detectors 5a, or as a matrix of detector elements 5b. In either case, the receiver is scanned in a linear fashion by the x-ray beam 4a; the receiver measuring the radiation issuing from the patient at each longitudinal increment of the scanning process. Every image line of the image reproduced on the television monitor 9 corresponds to the response of a transverse section of the array of long detectors 5a transversely to the longitudinal axis 1a of the support, or to the response of a transverse row 5c of detector elements 5b running transverse to the longitudinal axis 1a of the support. The first and last rows of detectors 5b (formed by individual detectors of the respective series-connected columns such as that shown in FIG. 3C) are designated 5c-l and 5c-N, to indicate that N sets of readings may be taken to provide N image lines on display 9. The number of image points per image line (n) is equal to the number of detector elements 5b per transverse row 5c. In the diagrammatic example, each transverse row 5c possesses fifteen detector elements 5b, and eleven detector elements 5b are present in each series arrangement such as 5b-l. In practice, however, these numbers are substantially greater in order to achieve a good image resolution.

The computer 8 contains a shadow image memory which stores each set of signals supplied by the radiation receiver 5 and corresponding to an image line, in the shadow image generating mode. After a complete scanning of the radiation receiver 5 in the longitudinal direction of the patient support 1 the entire x-ray shadow image is thus stored in the computer 8.

It is possible to arrange the diaphragm 10 in fixed relation to the x-ray tube 4 if said diaphragm, together with the x-ray tube is movably arranged in the longitudinal direction of the patient support 1. Also in this case, a line-by-line scanning of the radiation receiver 5 is possible. To this end the x-ray tube 4 and the diaphragms 10 and 11 are moved synchronously to effect a longitudinal scanning operation.

For every series of detector elements 5b, a single intensifier strip of x-ray luminescent material may extend adjacent thereto for measured value intensification. With series-connected detector elements in a matrix as in FIG. 3B, the horizontal lines at each side of each of the successive rows such as 5b-l and 5b-n may represent the edge of such a single intensifier strip. However, it is also possible to provide a separate intensifier for every detector element.

It will be apparent that many modifications and variations may be effected without departing from the scope of the novel concepts and teachings of the present invention.

SUPPLEMENTARY DISCUSSION

A beam longitudinal scanning means is indicated at 12 for coupling with the beam 4a to scan the same between an initial position as represented at 4a-l by the solid lines, and a final position as indicated by the dash lines at 4a-N. In the initial beam position 4a-l, the beam impinges on the first arcuate column 5c-l of the matrix of detectors as shown in FIG. 3B. The successive beam positions are aligned with the successive columns of the matrix, the final beam position 4a-N being aligned with column 5c-N, FIG. 3B.

In a first embodiment, the coupling line 12a may represent a mechanical coupling to the diaphragms 10, 11 such that at a first pulse of the x-ray source 4, the slits in diaphragms 10 and 11 are aligned with column 5c-l while covering the remaining columns. The diaphragms are of configuration to cover all but one column of detectors for each pulsing of source 4, and in the final position, the slits of the diaphragms 10, 11 are aligned with column 5c-N while covering all the preceding (N−l) columns.

In a second embodiment the coupling 12a may represent a rigid coupling with source 4 and diaphragms 10 and 11, so that all three move jointly to effect longitudinal scanning. In this case, the initial position of source 4 and the slits of diaphragms 10 and 11 may be perpendicular to the longitudinal axis 1a if desired so that the initial beam corresponding to 4a-l would be vertically directly above and aligned with column 5c-l.

By way of background, the disclosure of U.S. Pat. No. 4,174,481 issued Nov. 13, 1979 is incorporated herein by reference, said patent corresponding to German Auslegeschrift No. 26 13 809, and being assigned to the assignee of the present application. Said patent (at columns 5 and 6) describes an exemplary radiation receiver which is disclosed in further detail in a U.S. application Ser. No. 940,562 filed Sept. 8, 1978, assigned to the assignee of the present application. Said application Ser. No. 940,562 discloses in the third and fourth figures, a series of arcuately arranged semiconductor diodes with x-ray responsive fluorescent layers on each side of each semiconductor diode. For the embodiment of FIG. 3A where the semiconductor diodes 5a are elongated in the longitudinal direction, the fluorescent layers could be correspondingly elongated so that the lines on each side of the detectors 5a in FIG. 3A could represent the locations of fluorescent strips similar to the layers of said application. In the embodiment of FIG. 3B, the arcuate series of the third and fourth figures could be repeated N times to form the matrix of FIG. 3B, with the electrodes of the corresponding detectors of each arcuate series being connected as indicated in FIG. 3C.

I claim as my invention:

1. Tomographic apparatus for the production of transverse layer images of a radiography subject, comprising a patient support, a radiation measuring arrangement having a radiation source which generates a beam of rays which is fan-shaped in the layer plane, penetrating the radiography subject, whose cross sectional extent perpendicular to the layer plane is equal to the layer thickness, and a radiation receiver comprising a series of detector means, the series extending transversely to the longitudinal axis of the support so as to determine the radiation intensity at successive transversely offset points behind the subject, a rotating device for the measuring arrangement for rotation about an axis parallel to the longitudinal axis of the patient support, and a measured value converter for the conversion of the signals supplied by the radiation receiver into a tomographic image, means for the scanning of several parallel transverse layers and for the calculation and reproduction of an x-ray shadow image, whose length corresponds to the distance between the two exterior transverse layers and whose width corresponds to the width of the radiation receiver, characterized in that said detector means (5a, series connection 5b) of the radiation receiver each has an extent in a longitudinal direction parallel to the longitudinal axis of the support so as to provide for the formation of the x-ray shadow image by means of line-by-line scanning of the radiation receiver with the radiation (4a) issuing from the patient, in lines running perpendicularly to the longitudinal axis of the support, and characterized in that each detector means of the radiation receiver is formed as a series connection of a plurality of detector elements (5b), such that the radiation receiver (5) is formed from a matrix of detector elements (5b).

2. Tomographic apparatus according to claim 1, characterized in that, in order to move the x-ray beam in the longitudinal direction of the patient support (1), two slit diaphragms (10, 11) are present between which the patient can be inserted, and which are movable synchronously relative to one another for the purpose of moving a fan shaped beam (4a) for line-by-line scanning of the radiation receiver.

3. Tomographic apparatus according to claim 1, characterized in that, in order to move the x-ray beam (4a), the radiation source (4), together with a slit diaphragm (11), arranged beneath the patient support (1), is movable in such a manner that the radiation receiver (5) is scanned in line-by-line fashion by the x-ray beam (4a).

* * * * *